United States Patent [19]

Bando et al.

[11] Patent Number: 4,776,348
[45] Date of Patent: Oct. 11, 1988

[54] APPARATUS FOR DETERMINING MOTION OF JAW

[75] Inventors: Eiichi Bando; Tetsuya Fujimura, both of Tokushima, Japan

[73] Assignee: Shofu, Inc., Kyoto, Japan

[21] Appl. No.: 9,308

[22] Filed: Jan. 30, 1987

[30] Foreign Application Priority Data

Jan. 31, 1986 [JP] Japan .................................. 61-20904

[51] Int. Cl.⁴ .............................................. A61B 5/10
[52] U.S. Cl. .................................... 128/777; 323/208; 323/233
[58] Field of Search ................. 128/1.4, 1.5, 723, 774, 128/777, 782; 324/207, 208, 226, 227, 233, 234, 239, 260, 262, 236; 433/68, 69

[56] References Cited

U.S. PATENT DOCUMENTS

| | | | |
|---|---|---|---|
| 3,371,272 | 2/1968 | Stanton | 128/1.5 |
| 4,197,855 | 4/1980 | Lewin | 128/782 |
| 4,303,077 | 12/1981 | Lewin et al. | 128/777 |
| 4,386,405 | 5/1983 | Lewin et al. | 433/69 |
| 4,552,134 | 11/1985 | Binard | 324/233 |
| 4,595,022 | 6/1986 | Schorr | 128/777 |

Primary Examiner—Max Hindenburg
Attorney, Agent, or Firm—Robbins & Laramie

[57] ABSTRACT

An apparatus for accurately determining motion of a jaw without restricting its natural motion is disclosed. The apparatus comprises upper and lower jaw motion elements, at least two sensors and a phase detecting circuit. The sensors detect a phase of an alternating current induced within them.

9 Claims, 5 Drawing Sheets

APPARATUS FOR DETERMINING MOTION OF JAW

FIELD OF THE INVENTION

The present invention relates to an apparatus for determining the motion of a jaw. More particularly, it relates to an apparatus capable of accurately determining the motion of the upper and lower jaws without interfering a natural motion of the jaw.

BACKGROUND OF THE INVENTION

Japanese Patent Publication (unexamined) No. 89296/1978 discloses an apparatus for determining the motion of a jaw wherein the motion of the lower jaw is determined by a photosensor sensing light from a light source attached to the lower jaw. The photosensor of the apparatus is composed of light-receiving sensors, such as CCDs and phototransistors, which sense light from the light source. Accordingly, in order to enhance accuracy, it is required that the light-receiving sensors increase in number, but which makes the apparatus more expensive. Also, a calculation process and calculation circuit become complicated, since the direction of the light is changed to accompany the position change of the lower jaw. Further, in the apparatus mentioned above, when the head is moved together with the lower jaw, the motion of the head is also detected as the motion of the lower jaw. It, therefore, is required to fix the head, because the motion of the head causes determination errors. However, when one fully opens one's mouth, one has to raise the head up a little. Accordingly, it is difficult for the apparatus to carry out an accurate determination.

Japanese Utility Model Publication (unexamined) No. 34290/1979 discloses an apparatus which determines the motion of the lower jaw with three potentiometers. This apparatus has a complicated mechanism for transmitting the motion of the jaw to the potentiometers. Also a driving mechanism for the potentiometer has to have a play which causes determination errors. Further, since power is required to drive the potentiometers, it interferes with a natural motion of the jaw.

SUMMARY OF THE INVENTION

The present invention is to provide an apparatus for accurately determining the motion of the jaw without interfering with the motion of the jaw.

An important object of the present invention is to provide an apparatus for accurately determining the motion of the jaw wherein substantially no determination error owing to the motion of the head arises because of determining relative motion of the lower and upper jaw.

Another important object of the present invention is to provide a cheap apparatus which can accurately determine the motion of the jaw.

Accordingly, the apparatus of the present invention comprises (a) an upper jaw motion element attached to the upper jaw, (b) a lower jaw motion element attached to the lower jaw, (c) at least two sensors of which each sensor comprises a sensor coil attaching to either of said upper jaw motion element or said lower jaw motion element, and at least two field coils attaching to the other motion element, and (d) a phase detecting circuit for detecting a phase of an alternating current induced in said sensor coil by the function of said field coils, wherein alternating currents having a different phase are applied to said field coils to form an alternating current magnetic field between said field coils, an induced alternating current is formed in said sensor coil by the function of said alternating current magnetic field and its phase is changed according to the displacement of said sensor coil, and then the displacement of the sensor coil relative to the field coils is determined by said phase detecting circuit detecting the phase change of the induced alternating current.

BRIEF EXPLANATION OF THE DRAWINGS

FIG. 8(2) is a plot of induced voltage in a sensor coil over time.

FIG. 8(3) is a plot of the output of a waveform shaping circuit over time which is input to an exclusive OR circuit.

FIG. 8(4) is a plot of the output of a waveform shaping circuit over time which out of phase with Fig. 8(3).

FIG. 8(5) is a plot over time of an output of an exclusive OR circuit.

PREFERRED EMBODIMENT OF THE INVENTION

Figure 1:
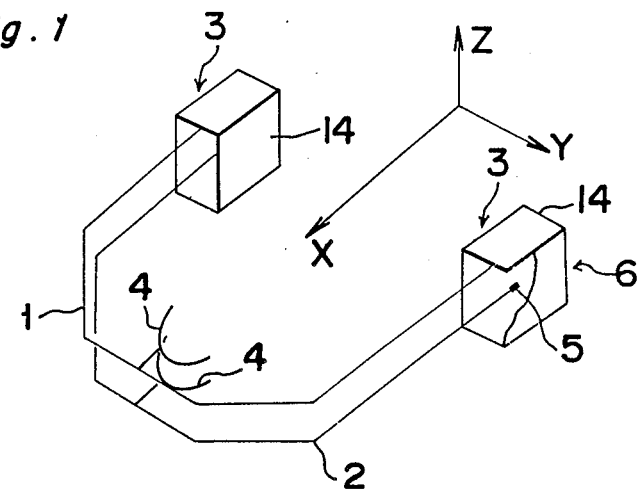
FIG. 1 is a perspective view schematically showing one embodiment of the apparatus of the present invention.
Figure 2:
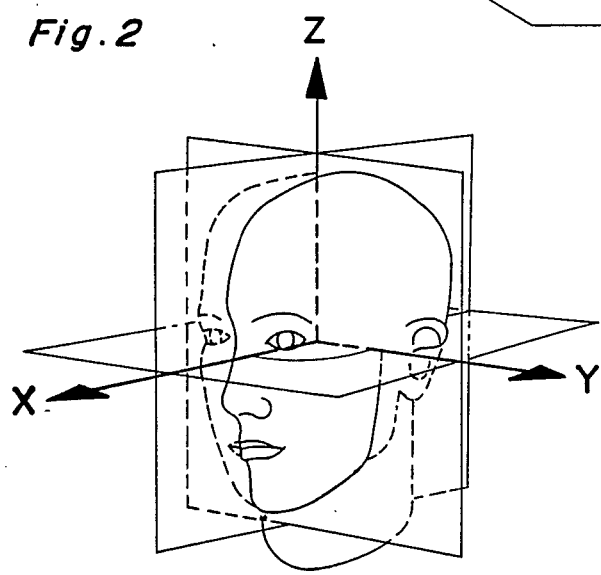
FIG. 2 is a perspective view showing X, Y and Z axes of the head.

In FIG. 1, the apparatus for determining the motion of the jaw is composed of an upper jaw motion element 1 attached to the upper jaw, a lower jaw motion element 2 attached to the lower element and a sensor 3 which is located at both ends of the upper and lower motion jaw and which detects the relative displacement of the jaw. The upper and lower jaw elements are bent to a U shape and both ends of the elements are positioned relative to the motion axis of the lower jaw, i.e. lower jaw joints located on the both sides of the face. At this position of the sensor, the displacement of the sensor becomes small even when the lower jaw is opened widely and therefore the sensor becomes lighter.

The upper jaw motion element 1 and the lower jaw motion element 2 are made from a light material. They are fixed to the upper jaw and lower lower jaw through an attachment element 4 which is gripped to the teeth. Examples of the light materials are light metals such as aluminum, synthetic resins, wood and the like.

The sensor 3 is composed of a sensor coil 5, field coils 6 and a phase detecting circuit 7. The sensor coil 5 is attached to either the upper jaw motion element 1 or the lower jaw motion element 2 and the field coils 6 are attached to the other motion element. In FIG. 1, the sensor coil 5 is attached to the lower jaw motion element 2 and the field coils 6 are attached to the upper jaw motion element 1.

The sensor coil 3 is at an end portion of the lower jaw motion element 2 and the coil of the sensor coil 3 is turned with a same direction as the motion element 2. The induced voltage becomes larger as the number of turns of the sensor coil 5 increases, but an increased number of turns makes the motion element 2 heavy. The preferred number of turns is generally 40 to 6,000.

The field coils 6 are positioned apart from the sensor coil 3 to avoid contact between the sensor coil 3 with the field coils 6. The field coils 6 are composed of coils 6A and 6B for detecting the displacement in the X direction of the sensor coil 3, coils 6C and 6D for detecting the displacement of Y direction of the sensor coil 3, coils 6E and 6F for detecting the displacement of Z direction of the sensor coil 3 and coils 6G an 6H for detecting the displacement of rotating angle r on Y axis.

Figure 3:
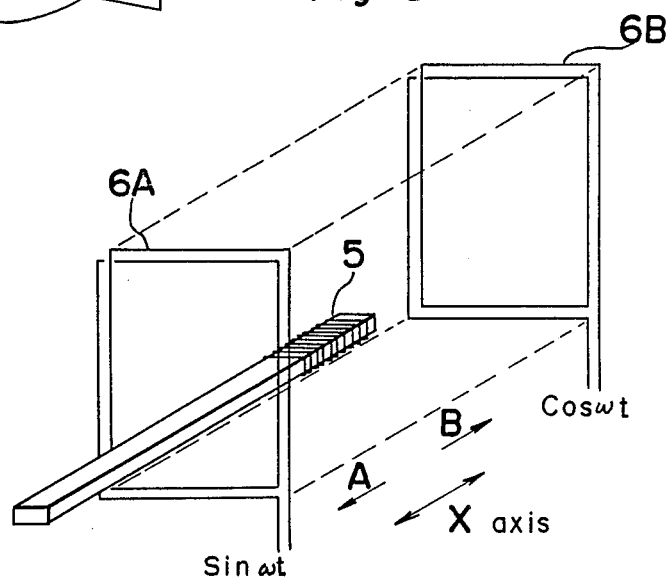
FIG. 3 is a perspective view schematically showing the position of the sensor coil and field coils for detecting displacement in the X direction.

As is shown in FIG. 3, the field coils 6A and 6B which is for detecting the displacement of X axis are positioned apart from the sensor coil 5 along with X axis. The field coils 6A and 6B are wound with the same direction as the sensor coil 5. The field coils 6A and 6B are respectively excited with two alternating currents having a phase difference of 90°. For example, an alternating current of E cos lt is applied to the field coil 6B and an alternating current of E sin lt is applied to the field coil 6A. If the sensor coil 5 is located at a center position between both field coils, an alternating current having a middle phase difference, i.e. $\cos(lt+\frac{1}{4})$, is induced in the sensor coil 5. If the sensor coil 3 moves to the A direction in FIG. 3, the induced current approaches to sin lt and if the sensor moves to B direction, the induced current approaches to cos lt. Accordingly, the displacement of the sensor coil 3 is detected from the induced current in the sensor coil 3. In order to ensure accuracy, it is required that the displacement should be corrected because the phase of the induced current is not linearly changed in proportion to the displacement of the X axis.

Figure 4:
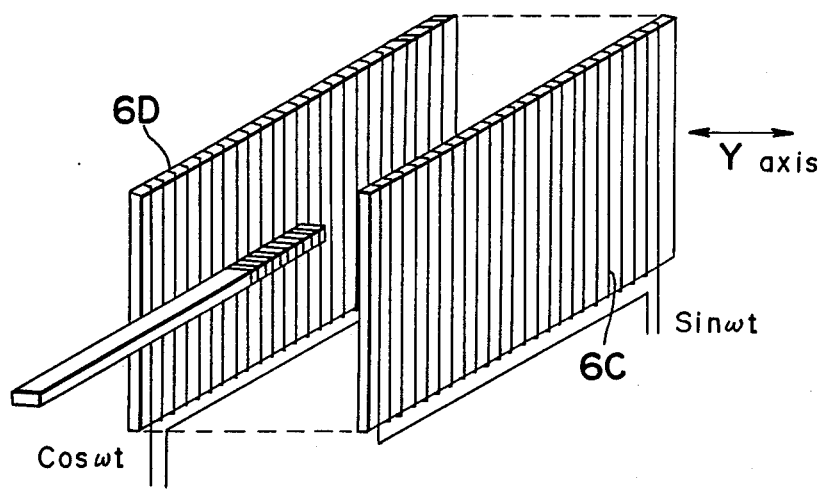
FIG. 4 is a perspective view schematically showing the position of the sensor coil and the field coils for detecting displacement in the Y direction.

The field coils 6C and 6D for detecting the displacement are positioned apart from the sensor coil 5 along with Y axis as shown in FIG. 4. The coils are wound with the same direction as the sensor coil 5. The field coil 6C and 6D are excited with alternating currents having a phase difference of 90°. If the sensor coil 5 is located at a center position between the both field coils, then an alternating current having $\cos(lt+\frac{1}{4})$ is induced in the sensor coil 5. If the sensor coil 3 moves to right, the induced current approaches to sin lt and if the sensor moves to the left, the induced current approaches to cos lt. Accordingly, the displacement of the sensor coil 3 can be detected from the phase change of the induced current in the sensor coil 3.

Figure 5:
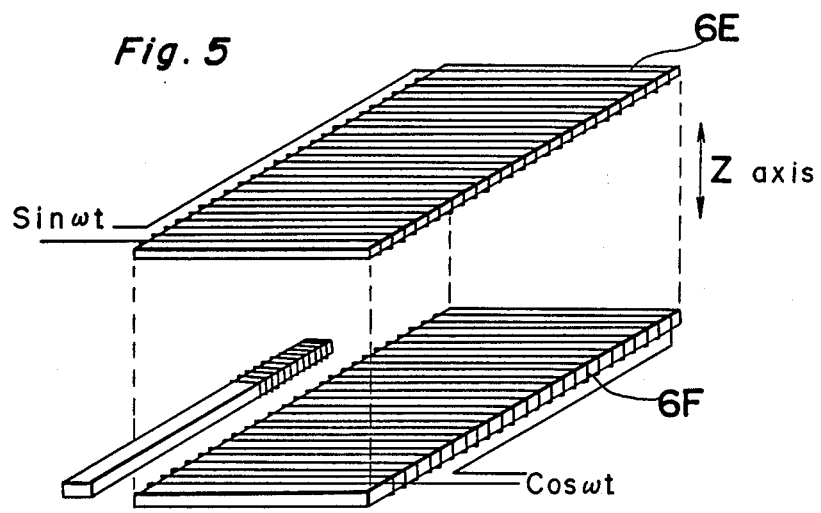
FIG. 5 is a perspective view schematically showing the position of the sensor coil and the field coils for detecting displacement in the Z direction.
Figure 6:
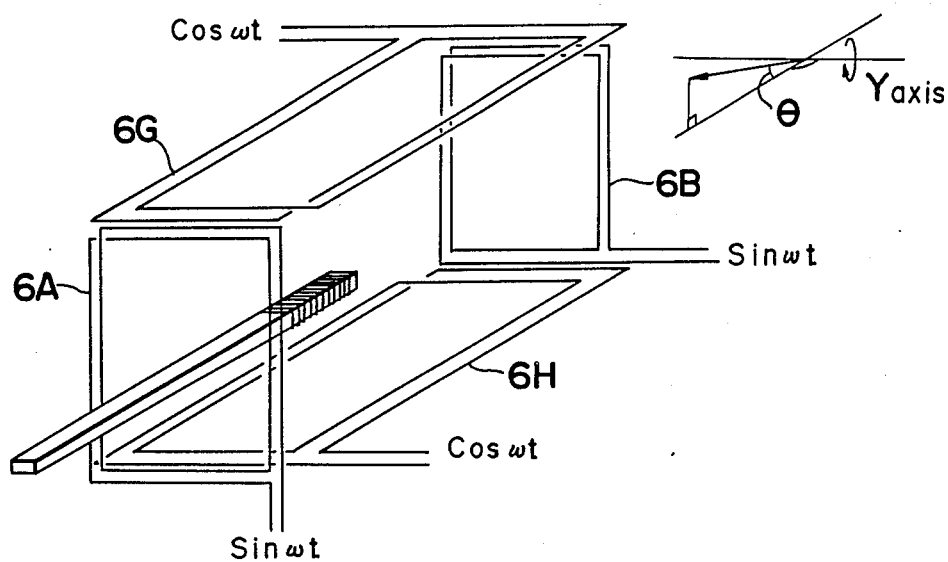
FIG. 6 is a perspective view schematically showing the position of the sensor coil and the field coils for detecting displacement of rotating angle r on the Y axis.

The field coils 6E and 6F for detecting the displacement are positioned apart from the sensor coil 5 along with Z axis as shown in FIG. 5. The coils are wound with the same direction as the sensor coil 5. The system for detecting the displacement of Z axis of the sensor coil 5 is the same as X axis.

In order to determine the motion of the jaw, a rotating angle on the Y axis may also be detected in addition to the detection of the displacement with X, Y and Z axes at both ends of the jaw. If the rotating angle is not measured, it is preferred that one more sensor is positioned in addition to both ends of the motion elements and a same detection is carried out with X, Y and Z axes.

For obtaining the rotating angle on the Y axis, the field coils 6A and 6B are used as one set of field coils and the field coils 6G and 6H positioned above and below the sensor coil 5 are used as the other set of field coils. The field coils 6A and 6B are excited with an alternating current having E sin lt and the field coils 6G and 6H are excited with an alternating current having E cos lt. When the sensor coil 5 is parallel to the X axis, an alternating current having sin lt which is the same phase as the field coil 6A and 6B is induced in the sensor coil 5. If the sensor coil 5 turns on the Y axis, the induced current shifts to the phase of cos lt.

The field coils 6 are attached to the inside of a case 14 opening one side from which the sensor coil 5 is inserted to the case 14. The case 14 is fixed to the upper jaw motion element 1 at an end.

Figure 7:
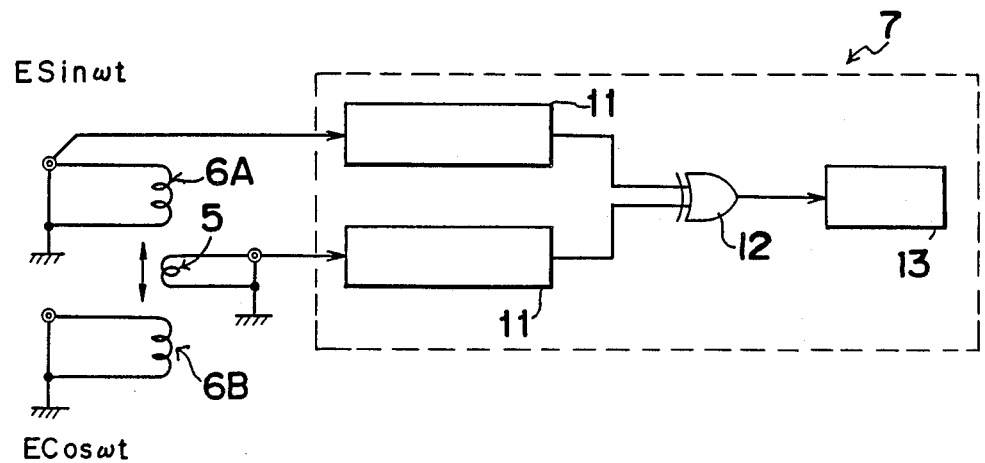
FIG. 7 is a block diagram showing one embodiment of the phase detecting circuit.
Figure 8:
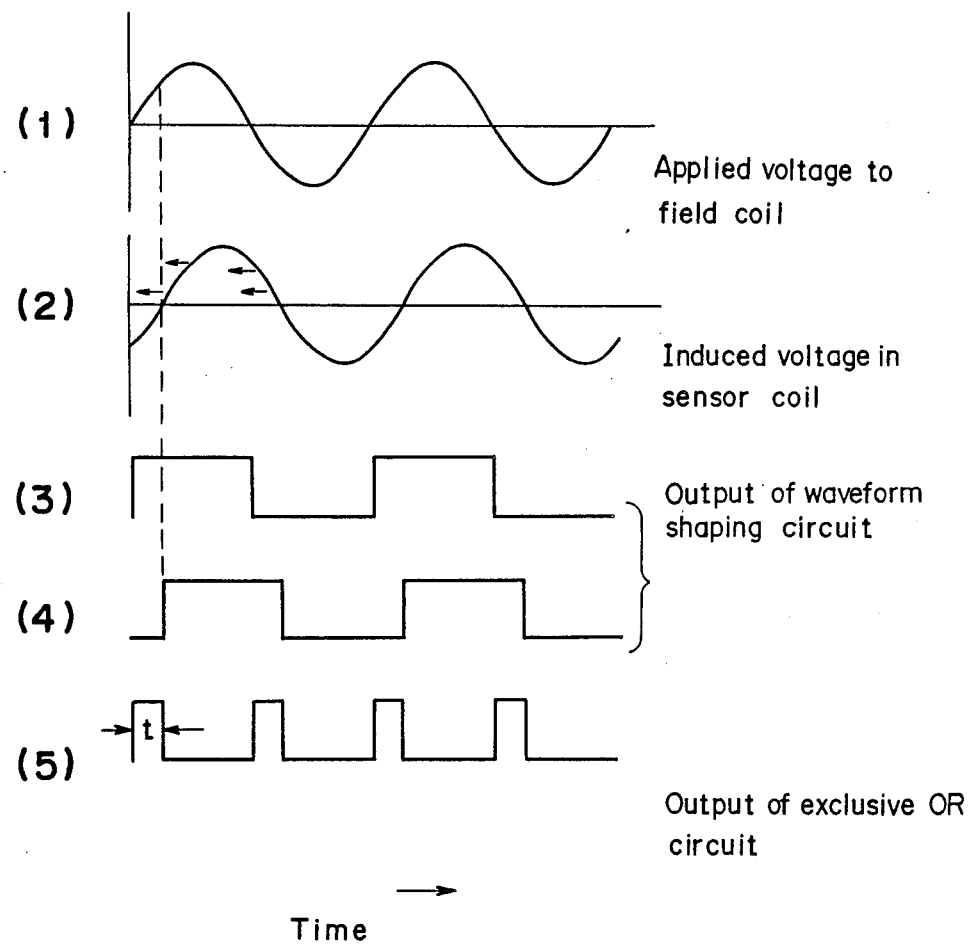
FIG. 8(1) is a plot of applied voltage to a field coil over time.

The phase difference of the induced current in the sensor coil 5 is detected by a phase detecting circuit 7. The phase detecting circuit is known to those skilled in the art. One example of the phase detecting circuit 7 is shown in FIG. 7. Waveforms in the detecting circuit 7 are shown in FIG. 8. In this phase detecting circuit, two alternating current input signals having phase difference (1) and (2) of FIG. 8 are shaped by a waveform shaping circuit 11 to rectangle waveform (3) and (4) which is input to an exclusive OR circuit 12. The exclusive OR circuit 12 makes a pulse signal being 1 when either of the inputted pulse has 1, as shown with (5) of FIG. 8, and the pulse width (t) which equals to phase difference is counted by a counter 13.

Figure 9:
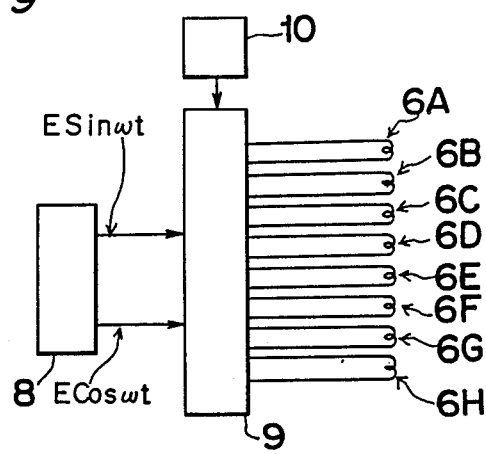
FIG. 9 shows an example of an oscillation generator.
Figure 10:
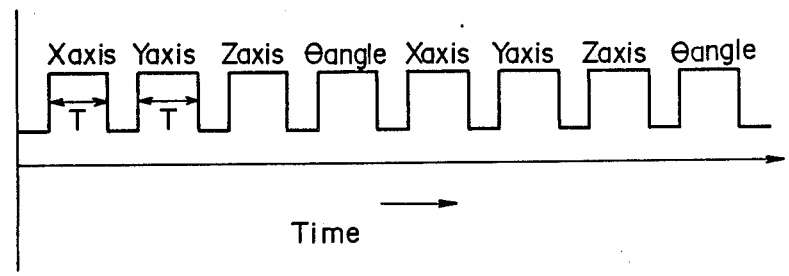
FIG. 10 is a timing chart diagram for determining X, Y and Z axes and angle r.
Figure 11:
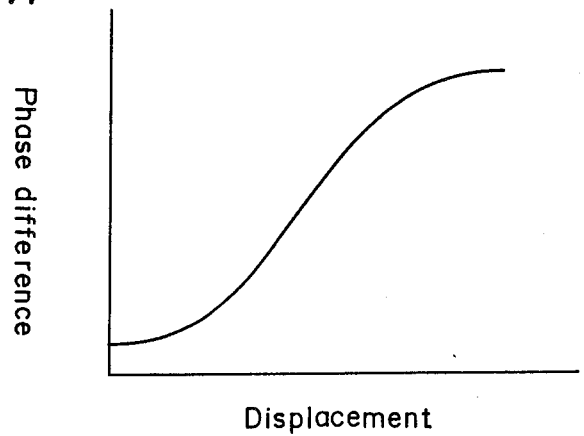
FIG. 11 is a graph showing displacement and phase difference.

The field coils 6 are excited by an oscillator which can output an alternating current having a phase difference having 90°. One example of the oscillator is shown in FIG. 9. One oscillator may control all sensors of the apparatus of the present invention or one oscillator may control only one sensor. The oscillator is composed of an oscillating circuit 8 generating two alternating currents i.e. E sin lt and E cos lt having the same frequency, a change over switch 9 changing the output of the oscillating circuit 8 to excite each of field coils 6A, 6B, 6C, 6D, 6E, 6F, 6G and 6H and a timer 10 periodically switching the change over switch 9. A timing chart for switching the change over switch is shown in FIG. 10. As appear from FIG. 10, a determination of displacement is carried out for a period of time (T) in the order of X, Y, Z and r. The period of time (T) is a period which is as quick as the motion of the jaw, and is generally adjusted to the range of 10 msec to 100 msec. The frequency of the alternating current applied to the field coils 6 is adjusted to 100 Hz to 100 KHz.

If an output time of the oscillator is regulated as shown in FIGS. 9 and 10, it is preferred that the phase detecting circuit 7 is also synchronized to the output time. Accordingly, it is preferred that the counter 13 of the phase detecting circuit 7 is also regulated by the timer 10.

As is not demonstrated in the drawings, more than two sensor coils can be employed to continuously obtain displacement of the jaw. In case of this, the field coils are fixed to the upper and lower jaw motion elements not to interfere with each other in magnetic force line.

Although the alternating currents which are applied to the field coils in the above embodiment have a phase difference of 90°, the phase difference can take any values other than 90°. But the smaller the phase difference, the worse the accuracy of the determination. Also, the sensors 3 are attached at both ends of the upper and lower jaw motion elements 1 and 2 in the above embodiment, but it is not limited. For example, three of the sensors 3 can be positioned at both ends of the elements 1 and 2 and at a position between the both ends. Also, the sensors can be attached at any positions between both ends.

What is claimed is

1. An apparatus for determining a motion of a jaw, comprising:
    (a) an upper jaw motion element attached to the upper jaw,
    (b) a lower jaw motion element attached to the lower jaw,
    (c) at least two sensors, each sensor comprising a sensor coil and an associated field coil, attached to either of said upper jaw motion element or said lower jaw motion element, such that each sensor coil and its associated field coil are not attached to the same motion element, the sensor coil and its associated field coil are movable in operative relationship to each other,
    (d) a source of alternating current for each field coil having a selected phase angle different from that of other field coils, each field coil for producing an induced current in its associated sensor coil, said induced current having a phase responsive to the displacement of the sensor coil relative to its associated field coil, and
    (e) a phase detecting circuit for detecting the phase of the alternating current induced in said sensor coil by the associated field coil.

2. The apparatus according to claim 1 wherein number of the sensors is two.

3. The apparatus according to claim 2 wherein each sensor is adapted to detect relative motion of the upper and lower jaw motion element in mutually perpendicular X, Y, and Z axes and relative rotational movement of an angle r about the Y axis and each sensor comprises 8 field coils in which two coils determine the X axis, two coils determine the Y axis, two coils determine the Z axis and four coils including the two coils for X axis and the remaining two coils determine the rotating angle r on the Y axis.

4. The apparatus according to claim 2 wherein the sensors are positioned at both ends of the upper and lower jaw motion elements.

5. The apparatus according to claim 1 wherein number of the sensors is three.

6. The apparatus according to claim 5 wherein each sensor is adapted to detect relative motion of the upper and lower jaw motion elements in mutually perpendicular X, Y, and Z axes and each sensor comprises 6 field coils in which two coils detect the X axis, two coils detect the Y axis and two coils detect the Z axis.

7. The apparatus according to claim 5 wherein two of the sensors are located at opposite ends of the upper and lower jaw motion elements and the other sensor is located between both ends of the jaw motion elements.

8. The apparatus according to claim 1 wherein the phase difference of the alternating currents is 90°.

9. The apparatus according to claim 1 wherein the phase detecting circuit comprises a waveform shaping circuit, an exclusive OR circuit and a pulse counter.

* * * * *